United States Patent
Lo et al.

(10) Patent No.: US 10,241,970 B2
(45) Date of Patent: Mar. 26, 2019

(54) REDUCED MEMORY NUCLEOTIDE SEQUENCE COMPARISON

(71) Applicant: Microsoft Technology Licensing, LLC, Redmond, WA (US)

(72) Inventors: Daniel Lo, Bellevue, WA (US); Eric Chung, Woodinville, WA (US); Kalin Ovtcharov, Kirkland, WA (US); Ravindra Pandya, Clyde Hill, WA (US); David Heckerman, Santa Monica, CA (US); Roman Snytsar, Sammamish, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 118 days.

(21) Appl. No.: 15/351,372

(22) Filed: Nov. 14, 2016

(65) Prior Publication Data
US 2018/0137085 A1    May 17, 2018

(51) Int. Cl.
*G06F 17/16* (2006.01)
*G06F 19/22* (2011.01)

(52) U.S. Cl.
CPC .............. *G06F 17/16* (2013.01); *G06F 19/22* (2013.01)

(58) Field of Classification Search
CPC .......... G06F 19/22; G06F 19/28; G06F 19/10; G06F 17/16
See application file for complete search history.

(56) References Cited

U.S. PATENT DOCUMENTS

| 9,014,989 | B2 | 4/2015 | McMillen et al. |
| 9,235,680 | B2 | 1/2016 | Rooyen et al. |
| 9,342,652 | B2 | 5/2016 | Van Rooyen et al. |
| 2012/0239706 | A1 | 9/2012 | Steinfadt |
| 2014/0025312 | A1 | 1/2014 | Chin et al. |

(Continued)

OTHER PUBLICATIONS

Nawaz, et al., "A Parallel FPGA Design of the Smith-Waterman Traceback", In IEEE International Conference on Field-Programmable Technology (FPT), Dec. 8, 2010, pp. 454-459.

(Continued)

*Primary Examiner* — Matthew D Sandifer
(74) *Attorney, Agent, or Firm* — The Watson I.P. Group, PLC; Vladan M. Vasiljevic

(57) ABSTRACT

Comparisons between two nucleotide sequences can be performed by customized integrated circuitry that can implement a Smith Waterman analysis in a reduced memory footprint, storing and referencing only individual portions, or subsections, of a two-dimensional matrix that is representative of the comparison between the two nucleotide sequences. As the backtracking proceeds, backtracking metadata corresponding to a cell from a subsection that is not currently retained in memory can be required. Such a subsection can be regenerated from previously generated scores associated with checkpoint cells of the two-dimensional matrix that comprise two edges of the subsection being regenerated. Moreover, to further reduce memory consumption, the backtracking metadata stored for each cell can comprise four binary digits: two indicative of a directional assignment, one indicative of whether the corresponding cell is part of a deletion stretching across multiple contiguous cells, and one analogously indicative of insertions stretching across multiple contiguous cells.

20 Claims, 8 Drawing Sheets

(56) References Cited

U.S. PATENT DOCUMENTS

| | | |
|---|---|---|
| 2014/0297196 A1 | 10/2014 | Olson |
| 2015/0106783 A1 | 4/2015 | Mytkowicz et al. |
| 2015/0199473 A1 | 7/2015 | Kural |
| 2017/0337325 A1* | 11/2017 | Olson .................... G06F 19/22 |

OTHER PUBLICATIONS

"International Search Report and Written Opinion Issued in PCT Application No. PCT/US2017/059141", dated Mar. 1, 2018, 16 Pages.

El-Wafa, et al., "Hardware Acceleration of Smith-Waterman Algorithm for short read DNA Alignment Using FPGA", In Proceedings of IEEE 40th Annual Computer Software and Applications Conference, Jun. 10, 2016, pp. 604-605.

Chang, et al., "Optimization Strategies for Smith-Waterman Algorithm on FPGA Platform", In Proceedings of International Conference on Computational Science and Computational Intelligence, Mar. 10, 2014, 8 pages.

Strengholt, et al., "Acceleration of the Smith-Waterman algorithm for DNA sequence alignment using an FPGA platform", In Thesis of Delft University of Technology, Jun. 27, 2013, pp. 1-60.

Pang, Alfred Yu-Han, "Implementation of the Smith-Waterman Algorithm on the Fleet Simulator", In Thesis of University of British Columbia, Feb. 2007, 34 pages.

McMohan, Peter Leonard, "Accelerating Genomic Sequence Alignment using High Performance Reconfigurable Computers", In Thesis of University of Cape Town, Oct. 2008, 82 pages.

Li, et al., "160-fold acceleration of the Smith-Waterman algorithm using a field programmable gate array (FPGA)", In Journal of BMC Bioinformatics, vol. 8, Issue 185, Jun. 7, 2007, 13 pages.

Harris, et al., "A Banded Smith-Waterman Fpga Accelerator for Mercury Blastp", In Proceedings of International Conference on Field Programmable Logic and Applications, Aug. 27, 2007, 5 pages.

Allred, et al., "Smith-Waterman Implementation on a FSB-FPGA module using the Intel Accelerator Abstraction Layer", In Proceedings of IEEE International Symposium on Parallel & Distributed Processing, May 23, 2009, 4 pages.

"Implementation of the Smith-Waterman Algorithm on a Reconfigurable Supercomputing Platform", In White Paper of Altera Corporation, Sep. 2007, pp. 1-18.

Sleibso, "OpenCL code compiled with Xilinx SDAccel accelerates genome sequencing, beats CPU/GPU performance/W by 12-21x", Published on: Feb. 10, 2016 Available at: https://forums.xilinx.com/t5/Xcell-Daily-Blog/OpenCL-code-compiled-with-Xilinx-SDAccel-accelerates-genome/ba-o/680764.

Okada, et al., "Accelerating the Smith-Waterman algorithm with interpair pruning and band optimization for the all-pairs comparison of base sequences", In Journal of BMC Bioinformatics, vol. 16, Issue 321, Oct. 6, 2015, 14 pages.

Houtgast, et al., "An FPGA-Based Systolic Array to Accelerate the BWA-MEM Genomic Mapping Algorithm", In Proceedings of International Conference on Embedded Computer Systems: Architectures, Modeling, and Simulation, Jul. 20, 2015, pp.

Ahmed, et al., "Heterogeneous Hardware/Software Acceleration of the BWA-MEM DNA Alignment Algorithm", In Proceedings of IEEE/ACM International Conference on Computer-Aided Design, Nov. 2, 2015, pp. 240-246.

\* cited by examiner

REDUCED MEMORY NUCLEOTIDE SEQUENCE COMPARISON

BACKGROUND

Specialized processing devices can comprise processing circuitry that is pre-configured to perform a discrete set of computing operations more quickly than generalized central processing units. Application-Specific Integrated Circuits (ASICs) comprise integrated circuitry that is specifically designed to perform a specific set of operations or calculations, and, as such, can perform such operations or calculations more quickly, or more efficiently, than generalized central processing units. Field-Programmable Gate Arrays (FPGAs) likewise comprise integrated circuitry, typically in the form of programmable logic blocks comprised of individual microprocessor gates and other like integrated circuits, which can be programmed or designed to perform a specific set of operations or calculations more quickly, and more efficiently, then generalized central processing units.

One area in which customized integrated circuits, such as ASICs and FPGAs, are utilized to perform calculations is in the analysis of nucleotide sequences. As will be recognized by those skilled in the art, two strings of nucleotide sequences can be compared such that the manner in which they align can reveal important differences. One mechanism for performing such a local sequence alignment is the Smith Waterman algorithm. Prior efforts to perform Smith Waterman analysis utilizing customized integrated circuits have been limited by the amount of memory required. Indeed, the traditional mechanism for comparing nucleotide sequences can require maintaining, in memory, a two-dimensional matrix that can consume several hundred kilobytes. While such a memory requirement is not, by itself, necessarily burdensome, it limits the number of pairs of nucleotide sequences that can be performed in parallel since each two-dimensional matrix, formed for the comparison of each pair of nucleotide sequences, consumes several hundred kilobytes. Existing solutions include storing such two-dimensional matrices in memory that is external to the customized integrated circuit performing the comparison of two strings of nucleotide sequences. However, as will be recognized by those skilled in the art, access to such memory can be substantially slower than access to memory located on a same chip, such as a same ASIC or FPGA whose circuitry is performing the comparison between the pair of nucleotide sequences.

SUMMARY

Comparisons between two nucleotide sequences can be performed by customized integrated circuitry that can implement a Smith Waterman analysis in a reduced memory footprint, storing and referencing only individual portions, or subsections, of a two-dimensional matrix that is representative of the comparison between the two nucleotide sequences. A first subsection, of the two-dimensional matrix, that is initially retained in memory can be a subsection comprising a cell from which backtracking can commence for purposes of generating a textual string comprising indicators of similarities and differences of the two nucleotide sequences. As the backtracking proceeds, backtracking metadata corresponding to a cell from a subsection that is not currently retained in memory can be required. Such a subsection can be regenerated from previously generated scores associated with checkpoint cells of the two-dimensional matrix that comprise two edges of the subsection being regenerated. In such a manner, backtracking can proceed through the entire two-dimensional matrix while only utilizing an amount of memory sufficient to store only a subsection of the two-dimensional matrix. Moreover, to further reduce memory consumption, the backtracking metadata stored for each cell can comprise a two-digit binary value indicative of a directional assignment associated with the corresponding cell, a first one-digit binary value indicative of whether the corresponding cell is part of a deletion stretching across multiple contiguous cells, and a second one-digit binary value indicative of whether the first cell is part of an insertion stretching across multiple contiguous cells.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Additional features and advantages will be made apparent from the following detailed description that proceeds with reference to the accompanying drawings.

DESCRIPTION OF THE DRAWINGS

The following detailed description may be best understood when taken in conjunction with the accompanying drawings, of which.

DETAILED DESCRIPTION

Figure 1:
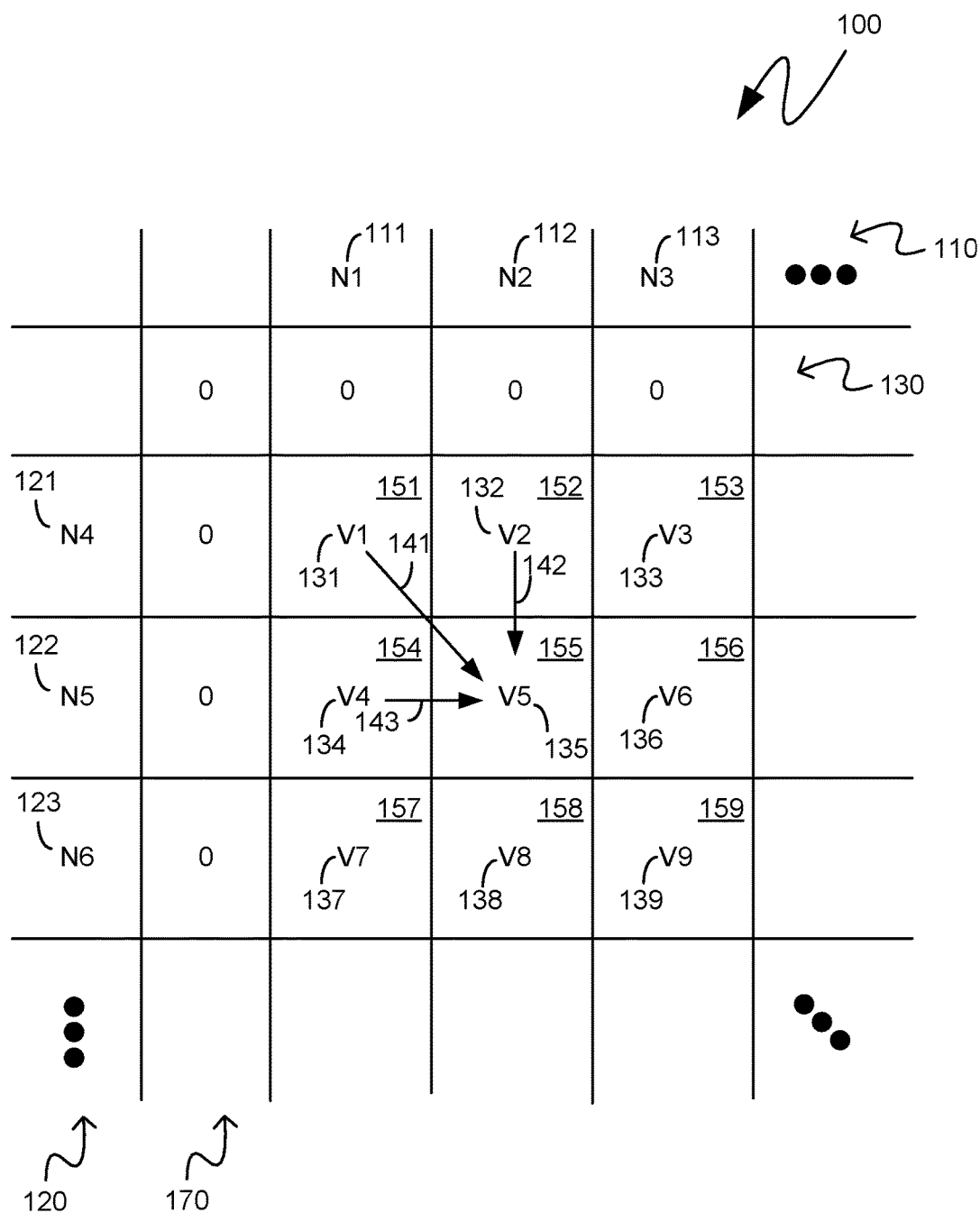
FIG. 1 is a block diagram of an exemplary two-dimensional matrix by which two nucleotides can be compared.

The following description relates to customized integrated circuitry that compares two strings of nucleotide sequences utilizing a Smith Waterman analysis in a reduced memory footprint by storing and referencing only individual portions, or subsections, of a two-dimensional matrix that is representative of the comparison between the two nucleotide sequences. A first subsection, of the two-dimensional matrix, that is initially retained in memory can be a subsection comprising a cell from which backtracking can commence for purposes of generating a textual string comprising indicators of similarities and differences of the two nucleotide sequences. As the backtracking proceeds, backtracking metadata corresponding to a cell from a subsection that is not currently retained in memory can be required. Such a subsection can be regenerated from previously generated scores associated with checkpoint cells of the two-dimensional matrix that comprise two edges of the subsection being regenerated. In such a manner, backtracking can proceed through the entire two-dimensional matrix while only utilizing an amount of memory sufficient to store only a subsection of the two-dimensional matrix. Moreover, to further reduce memory consumption, the backtracking metadata stored for each cell can comprise a two-digit binary value indicative of a directional assignment associated with the corresponding cell, a first one-digit binary value indicative of whether the corresponding cell is part of a deletion stretching across multiple contiguous cells, and a second one-digit binary value indicative of whether the first cell is part of an insertion stretching across multiple contiguous cells.

The techniques described herein make reference to the Smith Waterman analysis mechanism by which a pair of nucleotide strings can be compared to detect, and quantify, similarities and differences between them. However, the mechanisms described are not limited to that specific mechanism, and can be utilized with any other analogous mechanism for comparing two sequences of items, selected from an appropriately limited set of items, whereby their comparison detects and quantifies the similarities and differences between them.

As utilized herein, the term "customized integrated circuit" means processing circuitry that is specifically optimized to perform a discrete subset of computer processing operations, or execute a discrete subset of computer-executable instructions, such that a computing result is achieved in a shorter duration of processing time than the processing time within which a general-purpose central processing unit, which was not so specifically optimized, would have achieved the same computing result. Consequently, as utilized herein, the adjective "specifically optimized" means that, prior to performance of the discrete subset of computer processing operations, or prior to execution of the discrete subset of computer-executable instructions, by the customized integrated circuit, the physical circuitry of the customized integrated circuit is either configured, manufactured, or modified to perform the discrete subset of computer processing operations or execute the discrete subset of computer-executable instructions to the exclusion of other computer processing operations or other computer-executable instructions. Such configuration or modification can occur either before, or after, the customized integrated circuit has already been manufactured. By contrast, as utilized herein, the term "general-purpose central processing unit" means a central processing unit whose physical circuitry that implements logic functionality, as opposed to the physical circuitry that provides for temporary storage of binary data, remains invariant and can execute any computer-executable instructions programmed for such a central processing unit. Additionally, as utilized herein, the terms "processing unit" and "processing circuitry" mean a collection of one or more hardware circuits that is capable of executing computer-executable instructions or performing computer processing operations.

For purposes of illustration, exemplary customized integrated circuits can include Application-Specific Integrated Circuits (ASICs), Field Programmable Gate Arrays (FPGAs) or other Very Large Scale Integrated circuits (VLSIs). By way of a hardware-specific example, the gate arrays of an FPGA can have particular voltages applied to specific gates in order to configure those gates to perform logic operations that result in the performance of one or more specific computer processing operations, such as those computer processing operations that implement the scoring described below. Consequently, as utilized herein, the terms "computer-readable media" and "computer storage media", as explicitly defined below, include the circuitry of a customized integrated circuit. Similarly, the term "computer-executable instructions", as utilized herein, includes the configuration of circuitry, such as by establishing or applying specific voltages to specific circuit elements, that enables such circuitry to perform computer processing operations in accordance with such computer-executable instructions.

Although not required, some of the descriptions below will be in the general context of computer-executable instructions, such as program modules, being executed by a computing device, including, specifically, a computing device comprising, or having access to, one or more customized integrated circuits directed to the serial performance of Smith Waterman analysis, such as detailed below. More specifically, the description will reference acts and symbolic representations of operations that are performed by one or more computing devices or peripherals, unless indicated otherwise. As such, it will be understood that such acts and operations, which are at times referred to as being computer-executed, include the manipulation by a processing unit of electrical signals representing data in a structured form. This manipulation transforms the data or maintains it at locations in memory, which reconfigures or otherwise alters the operation of the computing device or peripherals in a manner well understood by those skilled in the art. The data structures where data is maintained are physical locations that have particular properties defined by the format of the data.

Generally, program modules include routines, programs, objects, components, data structures, and the like that perform particular tasks or implement particular abstract data types. Moreover, those skilled in the art will appreciate that the computing devices need not be limited to conventional personal computers, and include other computing configurations, including hand-held devices, multi-processor systems, microprocessor based or programmable consumer electronics, network PCs, servers, minicomputers, mainframe computers, and the like. Similarly, the computing devices need not be limited to stand-alone computing devices, as the mechanisms may also be practiced in distributed computing environments where tasks are performed by remote processing devices that are linked through a communications network. In a distributed computing environment, program modules may be located in both local and remote memory storage devices.

With reference to FIG. 1, an exemplary two-dimensional matrix 100 is illustrated by which a comparison between two nucleotides can be accomplished, such as in accordance with Smith Waterman analysis. The exemplary matrix 100 is illustrated within the context of a comparison between two strings of nucleotides, or nucleotide sequences, namely the exemplary string of nucleotides 110 and the exemplary string of nucleotides 120. As visually indicated by the ellipses, the exemplary nucleotide sequence 110 can comprise the exemplary nucleotide 111, followed by, in the exemplary nucleotide sequence 110, the exemplary nucleotide 112, which can, in turn, be followed by the exemplary nucleotide 113, and so on. In a similar manner, the exemplary nucleotide sequence 120 can comprise the exemplary nucleotide 121, followed by, in the exemplary nucleotide sequence 120, exemplary nucleotide 122, which can, in turn, be followed by the exemplary nucleotide 123, and so on. The exemplary two-dimensional matrix 100, therefore, has one of its two dimensions delineated by nucleotides of a first nucleotide sequence, such as the exemplary string of nucleotides 110, and further has the other of its two dimensions delineated by nucleotides of a second nucleotide sequence, such as the exemplary string of nucleotides 120.

According to one aspect, nucleotides can be one of: Adenine, often represented by the letter "A", Guanine, often represented by the letter "G", Cytosine, often represented by the letter "C" and Thymine, often represented by the letter "T". For the purpose of forming a double helix, A typically matches with T and G typically matches with C. In comparing two sequences of nucleotides, the Smith Waterman calculation compares only one side of the helix and, consequently, within that context, "matches" means identical nucleotides. For example, with reference to the exemplary nucleotide sequences 110 and 120, a match could be the nucleotide A in nucleotide strand 110 and the same nucleotide A in strand 120 in a corresponding position within the nucleotide strand.

One purpose of the exemplary matrix 100 is to quantify how well the nucleotide sequence 110 matches the nucleotide sequence 120. Such a quantification, in accordance with Smith Waterman mechanisms, is often referred to as a total Smith Waterman "score", and is reflective of the quantity of "matches", "insertions," and "deletions" when comparing nucleotide strings 110 and 120. Within the exemplary matrix 100, each cell, such as the cells 151, 152, 153, 154, 155, 156, 157, 159 and 159, can have generated for it a score that is representative of how well the two nucleotides, from the exemplary nucleotide sequences 110 and 120, corresponding to that cell, match one another. Row 130 and column 170, in the exemplary two-dimensional matrix 100, illustrate the base of "0" on which each row and column start when utilizing Smith Waterman mechanisms to compare two nucleotide sequences. The score of a cell can further be representative of how well prior nucleotides, in the nucleotide sequences 110 and 120, matched one another. The exemplary matrix 100 illustrates exemplary values for each of the cells 151, 152, 153, 154, 155, 156, 157, 159 and 159, namely the values 131, 132, 133, 134, 135, 136, 137, 138, and 139, respectively.

According to one aspect, the scores of an individual cell can be generated based on a maximum, from among different values, each being generated in accordance with a particular comparison or prior score. For example, with reference to the exemplary cell 151, the score 131, assigned to the exemplary cell 151, can be derived, at least in part, based on a comparison between the nucleotides, of the exemplary nucleotide sequences 110 and 120, that correspond to the exemplary cell 155, namely the nucleotide 121, from the exemplary nucleotide sequence 120, and the exemplary nucleotide 111, from the exemplary nucleotide sequence 110. If the aforementioned nucleotides 121 and 111, corresponding to the cell 151, match, then the cell can be assigned a score, or value, of "2". Conversely, if the nucleotides 121 and 111, corresponding to the cell 151, do not match, then a value of "−1" can be assigned, except that, according to one embodiment, the lowest score that can be assigned to any cell can be zero. Consequently, if the nucleotides 121 and 111, corresponding to the cell 151, do not match, then the cell 151 can be assigned a score of zero.

Subsequent cells of the exemplary matrix 100 can be generated in an analogous manner, except that they can also take into account the scores of previously generated cells. For example, and with reference to FIG. 1, an exemplary generation of a score 135, for the exemplary cell 155, is illustrated. More specifically, one aspect of the generation of the score 135, for the exemplary cell 155, is visually illustrated by the arrow 151, which can represent a determination of the score 135 that is based on the score 131, of the prior cell 141, in combination with a value indicative of whether or not the corresponding nucleotides, corresponding to the cell 151, namely the nucleotides 112 and 122, match one another. Such a value, indicative of whether the nucleotides 112 and 122 match, can be in accordance with the aforedescribed valuing system, whereby a match is assigned a value of "2", whereas a mismatch is assigned a value of "−1". Thus, for example, if the score 131, of the exemplary cell 151, was "2", due to the exemplary nucleotides 111 and 121, corresponding to the exemplary cell 151, matching one another, then the score 135, of the exemplary cell 155, in accordance with the calculation represented by the arrow 141, can be "4", if the corresponding nucleotides 112 and 122 match, or can be "1" if the corresponding nucleotides 112 and 122 do not match one another. More specifically, if the corresponding nucleotides 112 and 122 match, a value of "2", representing such a match, can be added to the exemplary score 131, yielding a score of "4" as the exemplary score 135 of the exemplary cell 155. Conversely, if the corresponding nucleotides 112 and 122 do not match, a value of "−1", representing such a mismatch, can be added to the exemplary score 131, yielding a score of only "1" as the exemplary score 135 of the exemplary cell 155.

As indicated previously, the calculation represented by the arrow 141 can be but one portion, or one aspect, taken into account in generating a score, or value, for a cell, such as exemplary score 135 for the exemplary cell 155. Other aspects are visually represented in the exemplary matrix 100 by the arrows 142 and 143. The calculation represented by arrow 142 can be the application, or addition, of a value, sometimes referred to as a "gap-scoring factor" to the score 132 of the cell 152, or any prior cell in the column above cell 155. If any of the calculations represented by the arrow 142 are found to yield a greater value, then than value becomes the score 135 of the cell 155. Typically, when this vertical calculation 142 yields the greatest result, it can be considered to be a delineation of a "deletion", where a nucleotide, or a string of nucleotides, in nucleotide sequence 120 are not present in nucleotide sequence 110 to which the nucleotide sequence 120 is being compared.

A determination represented by the arrow 143 can be similar to that described above in relation to arrow 142, in that a "gap-scoring factor" can be applied, or added to, the score 134 of the cell 154, or any previous horizontal cells in the row prior to cell 155. If any of the calculations represented by the arrow 142 are found to yield a greatest value, the score 135, of the cell 155, can be set to that value. When this horizontal calculation 143 yields the greatest result it can be a delineation of an "insertion", where a nucleotide, or string of nucleotides, in the nucleotide sequence 110 are not present in the nucleotide sequence 120 being compared to the nucleotide sequence 110.

The generation of scores of other cells of the exemplary matrix 100 can proceed in a like manner. For example, the generation of the score 139, of the cell 159, can be based on the largest of: (1) the score of a horizontally prior cell as added to a corresponding gap scoring factor, (2) the score of a vertically prior cell as added to a corresponding gap scoring factor or (3) the score of a diagonally prior cell as combined with the aforementioned similarity function. Thus, within the context of the cell 159, vertically prior cells can include cells whose scores, or values, were previously generated and which are in a same column of the exemplary matrix 100 as the cell 159, or, stated differently, cells that correspond to a same nucleotide 113, of the nucleotide sequence 110, as the cell 159. Similarly, within the context of the cell 159, horizontally prior cells can include cells who scores, values, were previously generated and which are in the same row of the exemplary matrix 100 as the cell 159, or, stated differently, cells that correspond to a same nucleotide 123, of the nucleotide sequence 120, as the cell 159. Lastly, in terms of the cell 159, a diagonally prior cell can be the cell 155, which can also be referred to as a "diagonally immediately prior cell".

Given the terminology as defined above, one aspect of the generation of the score 139 of the cell 159 can be the score 135 of the diagonally immediately prior cell, namely the cell 155, as combined with the aforementioned similarity function, which can add "2" to the score 135 if the nucleotides corresponding to the cell 159, namely the nucleotides 123 and 113, match one another, or which can add "−1" to the score 135 if the corresponding nucleotides 123 and 113 not match.

Another aspect of the generation of the score 139 can be the scores of vertically prior cells as combined with the aforementioned gap-scoring factor. For example, the score 136 of the immediately vertically prior cell 156 can be added to a gap-scoring factor associated with cell 156 for purposes of generating the score 139 of the cell 159. As another example, the score 133, of the vertically prior cell 153, can be added to a gap-scoring factor associated with the cell 153. According to one aspect, the gap-scoring factor associated with the cell 153 can be the same as the gap-scoring factor associated with the cell 156. According to another aspect, the gap-scoring factor associated with the cell 153 can be different from the gap scoring factor associated with the cell 156. As will be recognized by those skilled in the art, the gap-scoring factor can be user-selected based on various user-specific requirements in comparing the two nucleotide strings or sequences, such as user-specific requirements reflective of how tolerant the comparison is to be with respect to one or more nucleotides that are present in one nucleotide sequence, but not in the other. To generate the score 139, of the cell 159, the score 136 of the immediately vertically prior cell 156 can be added to the gap-coring factor associated with cell 156. That sum can then be compared to the score 133, of the vertically prior cell 153, as added to the gap scoring factor associated with that cell, namely the cell 153, and the largest of those two sums can then represent the portion of the score 139 derived from vertically prior cells. That portion, derived from vertically prior cells, can then be compared with the portion derived from the diagonally immediately prior cell in the manner detailed above. Again, the larger of the two can be selected as the score 139 of the cell 159.

A third aspect of the generation of the score 139 can be the scores of horizontally prior cells which, like the aforementioned vertically prior cells, can be combined with gap-scoring factors. For example, the score 138 of the immediately horizontally prior cell 158 can be added to a gap-scoring factor associated with cell 158 for purposes of generating the score 139 of the cell 159. As another example, the score 137, of the horizontally prior cell 157, can be added to a gap-scoring factor associated with the cell 157. As before, the gap-scoring factor associated with the cell 157 can be the same as, or different from, the gap-scoring factor associated with the cell 158 based on various user-specific requirements in comparing the two nucleotide strings or sequences. To generate the score 139, of the cell 159, the score 138 of the immediately horizontally prior cell 158 can be added to the gap-coring factor associated with cell 158. That sum can then be compared to the score 137, of the horizontally prior cell 157, as added to the gap scoring factor associated with that cell, namely the cell 157, and the largest of those two sums can then represent the portion of the score 139 derived from horizontally prior cells. That portion, derived from horizontally prior cells, can then be compared with the portion derived from the vertically prior cells as well as the portion derived from the diagonally immediately prior cell in the manner detailed above. The larger can be selected as the score 139 of the cell 159.

Figure 2:
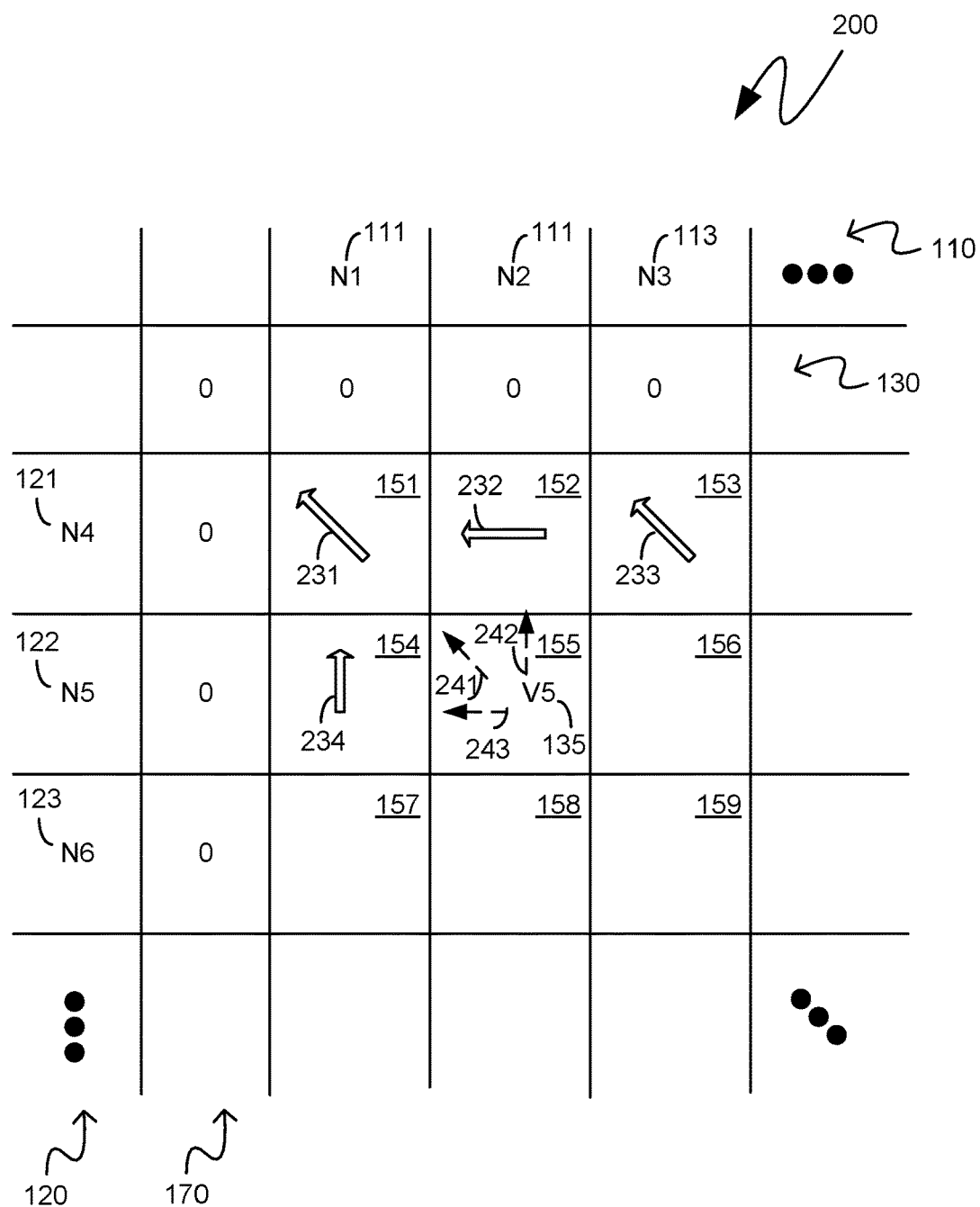
FIG. 2 is a block diagram of another aspect of an exemplary two-dimensional matrix by which two nucleotides can be compared.

Turning to FIG. 2, the exemplary matrix 200 illustrates one aspect of a "backtracking" process of within the context of the Smith Waterman algorithm. Together with the generation of scores of individual cells in the manner detailed above, a directional aspect can be assigned to each cell. These directional assignments, such as those illustrated by the arrows 231, 232, 233, and 234, in cells 151, 152, 153, and 154, respectively, can indicate which previous cell's score was used to generate the score of the cell having the directional assignment. More specifically, as indicated above, a portion of the score of a cell can be derived from horizontally prior cells, another portion can be derived from vertically pride ourselves, and a third portion can be derived from the diagonally immediately prior cell, and each of those portions can be compared to one another and the largest of the three can be selected as the score of the cell. Thus, for example, as detailed above with respect to FIG. 1, the score 135, of the cell 155, can be the larger of the calculation represented by the arrow 141, deriving from the diagonally immediately prior cell 151, the arrow 142 deriving from the vertically prior cell 152, and the arrow 143 deriving from the horizontally prior cell 154. If the above described calculations, represented by the arrow 141, deriving from the diagonally immediately prior cell 151, result in the highest value and, thereby, the score 135, of the cell 155, then, in FIG. 2, the cell 155 can have a directional assignment represented by the arrow 241, pointing to the diagonally immediately prior cell 151. Similarly, if the above described calculations, represented by the arrow 142, deriving from the vertically prior cell 152, result in the highest value and, thereby, the score 135, of the cell 155, then, in FIG. 2, the cell 155 can have a directional assignment represented by the arrow 242, pointing to the vertically prior cell 152. To complete the description, if the above described calculations, represented by the arrow 143, deriving from the horizontally prior cell 154, result in the highest value and, thereby, the score 135, of the cell 155, then, in FIG. 2, the cell 155 can have a directional assignment represented by the arrow 243, pointing to the horizontally prior cell 154.

In one aspect, a diagonal-left-and-upward directional assignment, such as that illustrated by arrow 231 in cell 151, can represent either a match in the corresponding cell 151 or a mismatch, such as the substitution of one nucleotide for another. Thus, as one example, the arrow 231, in cell 151, can be indicative of the match between the nucleotide 111, of the nucleotide sequence 110, and the nucleotide 121, of the nucleotide sequence 120, where the nucleotide 111 and the nucleotide 121 correspond to the cell 151. A horizontal right-to-left directional assignment, or a vertical upward directional assignment, can represent a non-match and the direction, either horizontal or vertical, can illustrate in which direction the highest weighting factor was taken from. In other words, the non-diagonal (vertical or horizontal) arrow can show in which direction there are more diagonal arrows. In such an aspect, a vertical directional assignment can represent a deletion, which, as defined previously, can be a nucleotide present on the nucleotide string 120 that is not present on the nucleotide string 110. Analogously, a horizontal directional assignment can represent an insertion, which, again, as defined previously, can be a nucleotide present on the nucleotide string 110 that is not present on the nucleotide string 120. In the exemplary matrix 200 shown in FIG. 2, cells 151, 152, 153, and 154 can have had their corresponding directional assignments, represented by arrows 231, 232, 233, and 234, respectively, already calculated.

Figure 3:
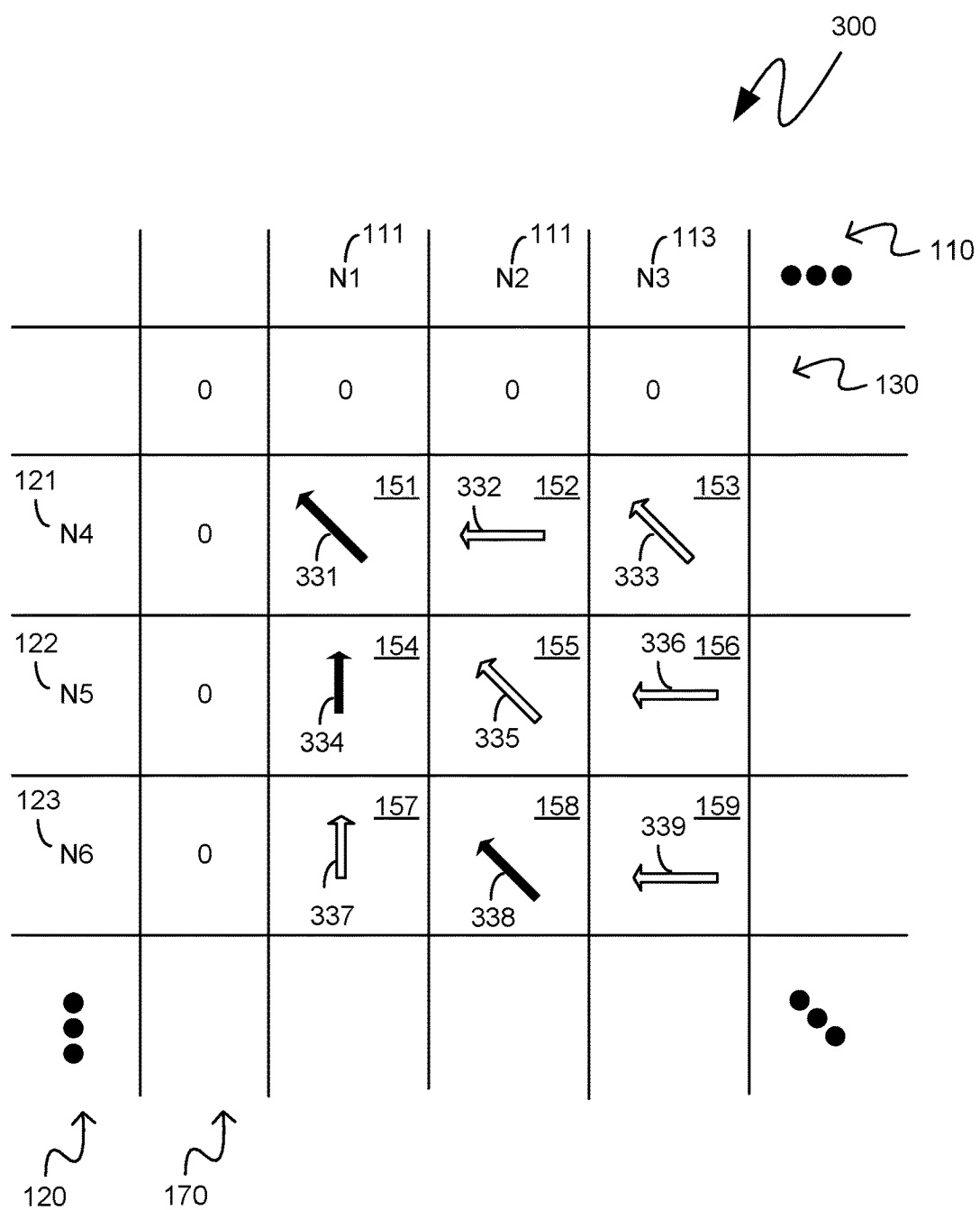
FIG. 3 is a block diagram of yet another aspect of an exemplary two-dimensional matrix by which two nucleotides can be compared.

According to one aspect, the directional assignments of the individual cells of the two-dimensional matrix, such as those illustrated in the exemplary matrix 200 of FIG. 2, can be utilized to generate an optimal alignment between the nucleotide sequence 110 and the nucleotide sequence 120 that are being compared to one another. Turning to FIG. 3, the exemplary matrix 300 shown therein illustrates an exemplary determination of such an optimal alignment. Initially, an optimal alignment can commence with a cell having a highest score in the two-dimensional matrix. Subsequently, the directional assignments of the cells of the matrix two-dimensional matrix can be utilized to "backtrack" across the matrix and, thereby, identify an optimal alignment. For example, a backtrack across the exemplary matrix 300 can commence at cell 158, as visually represented by the darkened arrow 338. The arrow 338 can represent a directional assignment of the cell 158, such as in the manner detailed above, and can identify the cell 154 as a next cell in the backtrack. Similarly, the arrow 334, visually representing a directional assignment of the cell 154, can identify the cell 151 as a next cell in the backtrack. Consequently, in exemplary matrix 300, the backtrack can follows the darkened arrows 338, 334, and 331, in that order, thereby identifying the cells 158, 154 and 151, respectively, as part of an optimal alignment between the nucleotide sequence 110 and the nucleotide sequence 120. From such a backtrack textual string comprising indicators of similarities and differences between two nucleotide strings can be generated in a manner well known to those skilled in the art. Such a textual string is typically referred to as a "CIGAR string" and provides textual indicators of a quantity of nucleotides that are similar, a quantity of nucleotides that are inserted, or deleted, and the relative locations of those groupings of nucleotides within a nucleotide sequence.

The exemplary matrix 300, shown in FIG. 3, also comprises non-darkened arrows 332, 333, 335, 336, 337, and 339, which are visually representative of directional assignments that were calculated, such as in the manner detailed above, but, however, as the system backtracked, it was determined that those directional assignments did not represent an optimal alignment. Nevertheless, traditional mechanisms for backtracking through a matrix, such as the exemplary matrix 300, require that the entire matrix be stored in memory prior to the commencement of the backtracking procedure, even though, as shown in FIG. 3, substantial portions of that matrix may never be utilized as part of the backtracking.

According to one aspect, therefore, only a portion of the two-dimensional matrix can be stored in memory, and other portions, or subsections, thereof can be regenerated as they are needed, if they are needed at all. More specifically, like the cells 152, 153, 155 and 156, of the exemplary matrix 300 of FIG. 3, the directional assignments of the cells of the two-dimensional matrix 300 may end up pointing to an optimal alignment that does not pass through that subsection of the two-dimensional matrix 300 that comprises the cells 152, 153, 155 and 156, in which case that subsection, to the extent it was not initially stored in memory, would never need to be regenerated.

Figure 4:
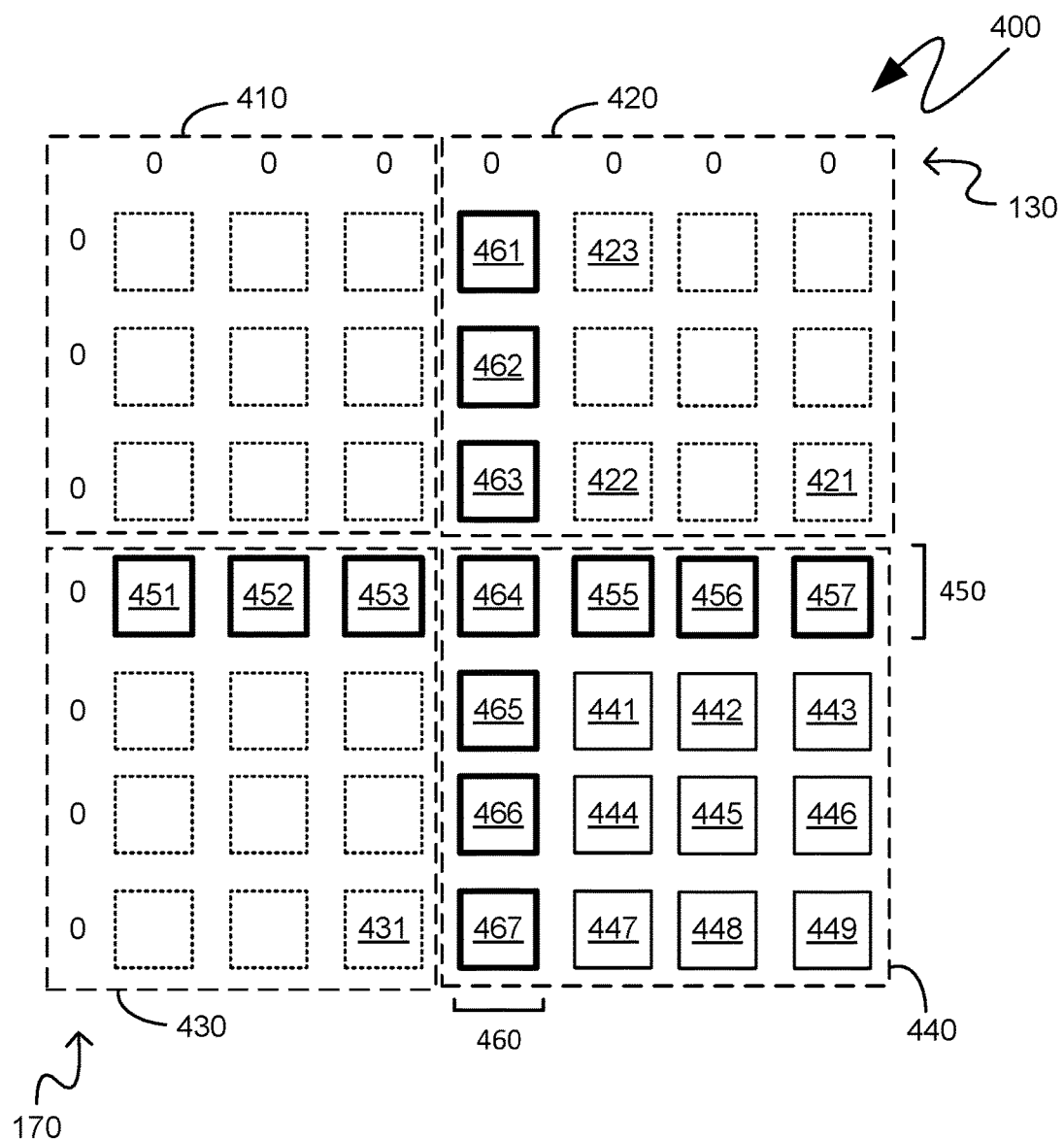
FIG. 4 is a block diagram of exemplary checkpoint cells in a two-dimensional matrix.

Turning to FIG. 4, an exemplary matrix 400, shown therein, illustrates mechanisms by which only subsections of a two-dimensional matrix can be stored for purposes of backtracking through the two-dimensional matrix. By storing only a portion, or subsection, the two-dimensional matrix, the mechanisms described herein can consume far less memory than traditional mechanisms. More specifically, the reduced memory requirements can enable the subsections of multiple matrices to be stored simultaneously, even within the limited storage capacity of memory located on a same chip as the customized integrated circuits implementing the mechanisms described herein. Consequently, such chips can enable multiple comparisons to be instantiated, and performed, in parallel from on-chip memory, whose access can be orders of magnitude faster than off-chip memory.

With reference to exemplary two-dimensional matrix 400 shown in FIG. 4, the exemplary two-dimensional matrix 400 can be divided into multiple subsections, such as the exemplary subsections 410, 420, 430 and 440. According to one aspect, backtrack metadata for the cells for only one of the subsections can be retained in memory. As will be described further below, backtrack metadata can comprise the directional assignments of the cells, detailed above, as well as other backtrack metadata. Initially, backtrack metadata for the cells of the subsection comprising a cell whose score was larger than the scores of all of the other cells of the two-dimensional matrix 400 can be stored in memory. Thus, for example, if the cell 421 was found to have the largest score among all of the cells in the exemplary two-dimensional matrix 400, the backtrack metadata of the cells of the subsection 420 can be initially stored in memory. As another example, if the cell 431 was found to have the largest score among all of the cells in the exemplary two-dimensional matrix 400, the backtrack metadata of the cells of the subsection 430 can be initially stored in memory. Commencing, then, with the cell having the largest score among all of the cells in the exemplary two-dimensional matrix 400, a backtracking procedure can proceed in accordance with the directional assignments of the cells whose backtrack metadata is stored in memory until a backtrack metadata of a cell of a subsection that is not stored in memory is required. At that point, that subsection can be regenerated.

By way of a more detailed example, if the cell 449 was found to have the largest score among all of the cells in the exemplary two-dimensional matrix 400, a backtracking procedure can commence with the cell 449, and then proceed as detailed above in accordance with the directional assignments, or other backtrack metadata, of the cells in the subsection 440, whose backtrack metadata can be stored in memory. Continuing with the example, if the backtracking procedure determines that cell 455 is part of an optimal alignment, and comprises, for example, a directional assignment pointing upward and identifying cell 442, a determination can be made that there is no backtrack metadata currently stored in memory for the cell 442, because the cell 442 can be part of the subsection 420, as opposed to the subsection 440 whose cells' backtrack metadata is currently stored in memory. Consequently, the backtrack metadata for cells of the subsection 420 can be regenerated.

As detailed above, scores for cells, such as in accordance with the Smith Waterman algorithm, can be generated based upon the scores of prior cells, including horizontally prior cells, vertically prior cells, and an immediately prior diagonal cell. For this reason, an exemplary two-dimensional matrix can be initialized with an initial row and column having a initial values, such as the zeros of the exemplary row 130 and column 170 described above, and again shown in FIG. 4. But the processing described previously can be equally applied to cells other than at the periphery of the exemplary two-dimensional matrix 400 so long as the values, or scores, of prior cells are known. Thus, for example, the scores of the cells in the subsection 420, and, correspondingly, their backtrack metadata, can be generated from the row 130 that was initialized with zeros and, instead of the column 170, with the values of the cells 461, 462 and 463. Accordingly, to regenerate the scores, and backtrack metadata, of the cells of the subsection 420, it can be sufficient to have retained only the scores of the cells 461, 462 and 463.

Once the backtrack metadata of the cells in the subsection 420 is regenerated, the backtracking procedure can proceed in the manner detailed above, except that, again, once it requires the backtrack metadata of the cell whose backtrack metadata is not currently stored in memory, another regeneration of such backtrack metadata of the cells in the subsection in which that cell is found, can be triggered. In such a manner, the backtrack metadata of the cells of only a portion, or subsection, of the exemplary two-dimensional matrix 400 need to be stored in memory at any given point in time. Moreover, once backtracking "leaves" a subsection, it may not require any further backtrack metadata from any other cells in that subsection. Consequently, according to one aspect, the same memory can be reused such that, as the backtrack metadata for the cells of one subsection is regenerated, the backtrack metadata of cells of a prior subsection can be overwritten.

As can be seen, therefore, in order to perform a backtracking procedure, it can be sufficient to retain the backtrack metadata of the cells of an initial subsection of a two-dimensional matrix that comprises the cell that has the largest score, among all of the cells of the two-dimensional matrix, as well as the scores for cells along the boundaries of the subsections, while the backtrack metadata and scores of the other cells, generated during an initial forward pass that resulted in the determination of which sell has the largest score, can be discarded and not retained in memory. For ease of reference, cells along boundaries of subsections, whose scores are retained, will be referred to hereinafter as "checkpoint cells". For example, FIG. 4 illustrates checkpoint cells 451, 452, 453, 464, 455, 456 and 457 which are all part of the checkpoint row 450, as well as checkpoint cells 461, 462, 463, 464, 465, 466 and 467 that are all part of the checkpoint column 460. As can be seen, checkpoint cells 461, 462 and 463 comprise a boundary column of the subsection 420, while checkpoint cells 451, 452 and 453 comprise a boundary row of the subsection 430. And, analogously, checkpoint cells 464, 465, 466, 467, 455, 456 and 457 comprise a boundary row and column of subsection 440.

According to one aspect, and as visually shown in FIG. 4, checkpoint cells can be those cells that are at the leftmost and/or uppermost boundaries of a subsection. Thus, for example, if it was the subsection 440 whose cells needed to have their backtrack metadata regenerated, such as if the exemplary two-dimensional matrix 400 extended further right and down beyond that shown in FIG. 4 and backtracking procedure had started in a not-illustrated subsection and had then selected one of the cells of the subsection 440, the cells of the subsection 440 can have their scores, and backtrack metadata, generated in the same way as described in detail above with reference to FIGS. 1 and 2, except that, instead of starting from an initial row and column having values of "0", as was the case in the exemplary matrices of FIGS. 1 and 2, the generation of such scores, and backtrack metadata, can start with the scores of the checkpoint cells 464, 455, 456, 457, 465, 466 and 467. For example, the score of the cell 441 can be generated based on the score of the cell 464, and the nucleotides corresponding to the cell 441, as well as based on the scores of the cells 455 and 465, with appropriate weighting factors added thereto, all of which in the same manner as detailed above.

A size of a two-dimensional matrix comparing to strings of nucleotide sequences can be based on the quantity of nucleotides in each sequence. According to one aspect, therefore, such a two-dimensional matrix can be subdivided into subsections, such as the exemplary subsections shown in FIG. 4, based on a maximum amount of available memory into which such subsections are to be stored. For example, if an amount of memory assigned to the performance of the aforedescribed nucleotide sequence comparisons was sufficient to store a 50×50 matrix, then the two-dimensional matrix could be subdivided such that each subdivision is a 50×50 matrix. Subdivisions at the periphery of the two-dimensional matrix can comprise leftover cells in the event that the quantity of rows or columns is not evenly divisible by the quantity of rows and columns in an appropriately sized subdivision. Those subdivisions of the two-dimensional matrix comprising the leftover cells and, consequently, being of a smaller size than the other subdivisions can be those subdivisions that are oriented most closely to the initial row and column of zeros. As such, the initial subdivision, or the subdivision whose cells' backtrack metadata is initially stored in memory, can be a subdivision that is sized in accordance with the amount of memory available. One mechanism by which a quantity of rows and columns in a subdivision can be determined is through modulo arithmetic, which can be performed very efficiently by modern processing units.

As visually shown in FIG. 4, according to one aspect, the subdivisions can be mutually exclusive. As utilized herein, the adjective "mutually exclusive", as applied to subdivisions of a two-dimensional matrix, means that every cell of one subdivision is part of only that subdivision, and is not part of any other subdivision. According to another aspect, however, certain cells, such as boundary cells, can be shared among subdivisions, such as, for example, to speed up the regeneration of backtrack metadata, or otherwise provide a double check on existing backtrack metadata.

As indicated previously, backtrack metadata can comprise the directional assignments indicative of how scores for individual cells were generated. In addition, backtrack metadata can comprise additional information for backtracking through the two-dimensional matrix. For example, backtrack metadata can include values indicative of a quantity of cells whose directional assignments are to be ignored, or skipped over, along a given direction. As will be recognized by those skilled in the art, such backtrack metadata can group together insertions or deletions since one insertion or deletion comprising multiple nucleotides can be more advantageous than multiple insertions or deletions comprising fewer, or only a single, nucleotide. However, such backtrack metadata can increase memory requirements, since such skip values can often be sufficiently large that several bits are required to store such backtrack metadata for each cell.

Figure 5:
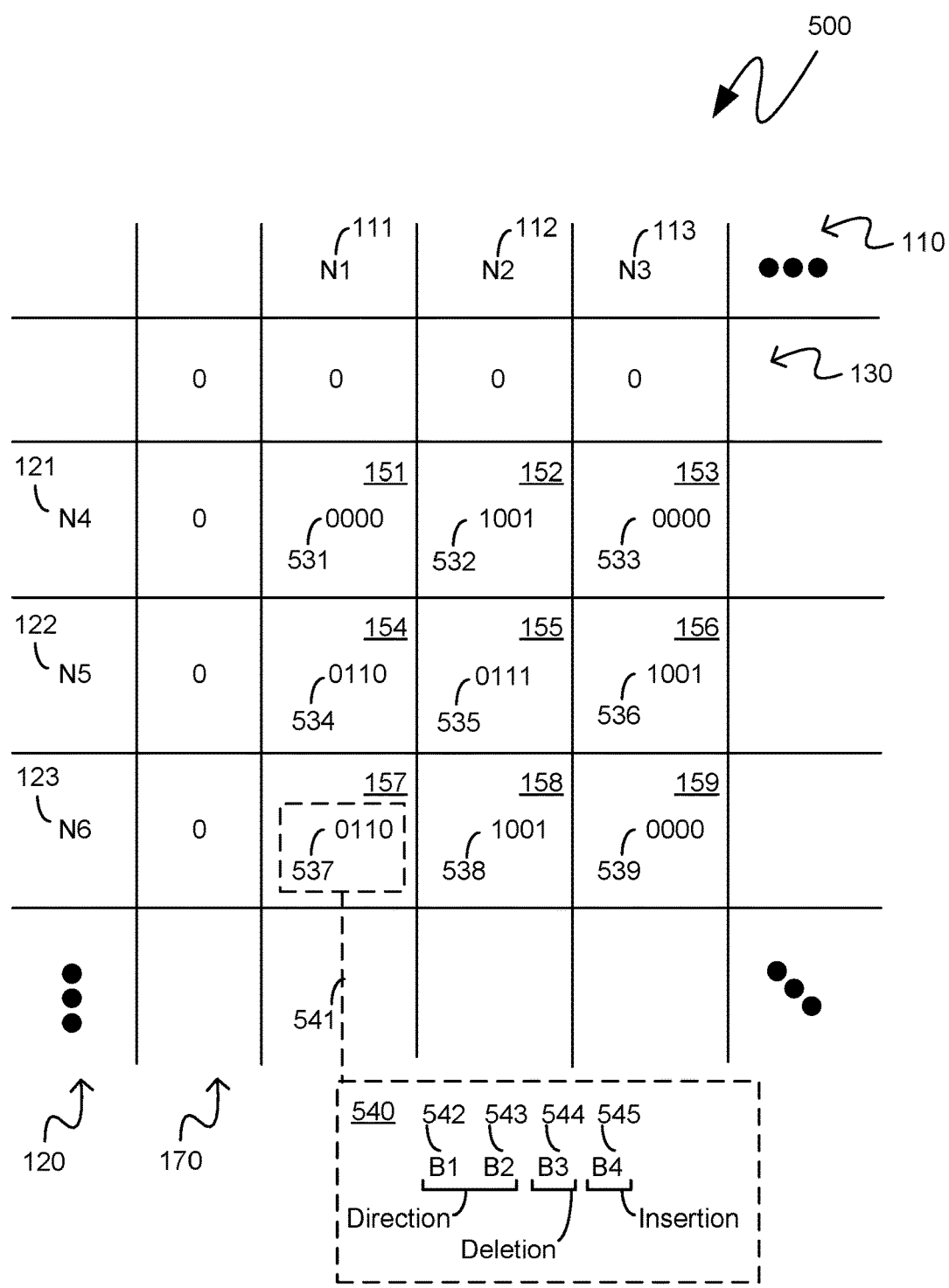
FIG. 5 is a block diagram of an exemplary backtracking metadata in a two-dimensional matrix.

Turning to FIG. 5, an alternative backtrack metadata comprising only four bits, is illustrated with reference to the exemplary two-dimensional matrix 500, showing exemplary four-bit backtrack metadata in each of the cells 151, 152, 153, 154, 155, 156, 157, 158 and 159, namely the exemplary backtrack metadata 531, 532, 533, 534, 535, 546, 537, 538 and 539, respectively. In exemplary call out 540, delineated by line 541, originating in cell 157, an aspect of how the four-bits can be used is visually illustrated. In the aspect shown in call out 540, the first two bits, namely bits 542 and 543 can represent the direction of the directional assignment, namely: diagonal, vertical, or horizontal. As those of skill in the art will recognize, since there are three possible directions, two bits are required to uniquely represent any specific one of the three possibilities. Binary value 544 can represent if the corresponding cell is part of a contiguous string of deletions and when that string of contiguous string of deletions has ended. For example, the backtrack metadata can indicate that an optimal alignment between the exemplary nucleotide sequence 110 and the exemplary nucleotide sequence 120 can proceed vertically upward from cell 157 to cell 154, representing a first deletion, and can then continue to proceed vertically upward from cell 154, to cell 151, representing a second deletion contiguous with the first deletion. Such backtrack metadata can specify such a two sequence deletion even if the directional assignment associated with the cell 154 does not in and of itself specify such a deletion. In such an instance, the deletion bit 544 can be "set", or can have a value of "1", for example, until such a multi-nucleotide deletion ends, which ending can be signified by the bit having a value of "0". In an analogous manner, the binary value 545 can identify whether a cell is part of a contiguous string of insertions and, again, by having an opposite binary value, when that string of contiguous insertions has ended. As detailed previously, these contiguous insertions or deletions are used to determine which "path" to follow to determine and optimal alignment between two nucleotide sequences, which can then be expressed in the form of a CIGAR string.

The exemplary binary values in exemplary matrix 500 were selected strictly by way of illustration, since, as those of skill in the art will recognize the opposite binary values can be assigned the same meanings as detailed above, with respect to the exemplary binary values utilized above, without departing from the scope of the descriptions.

Figure 6:
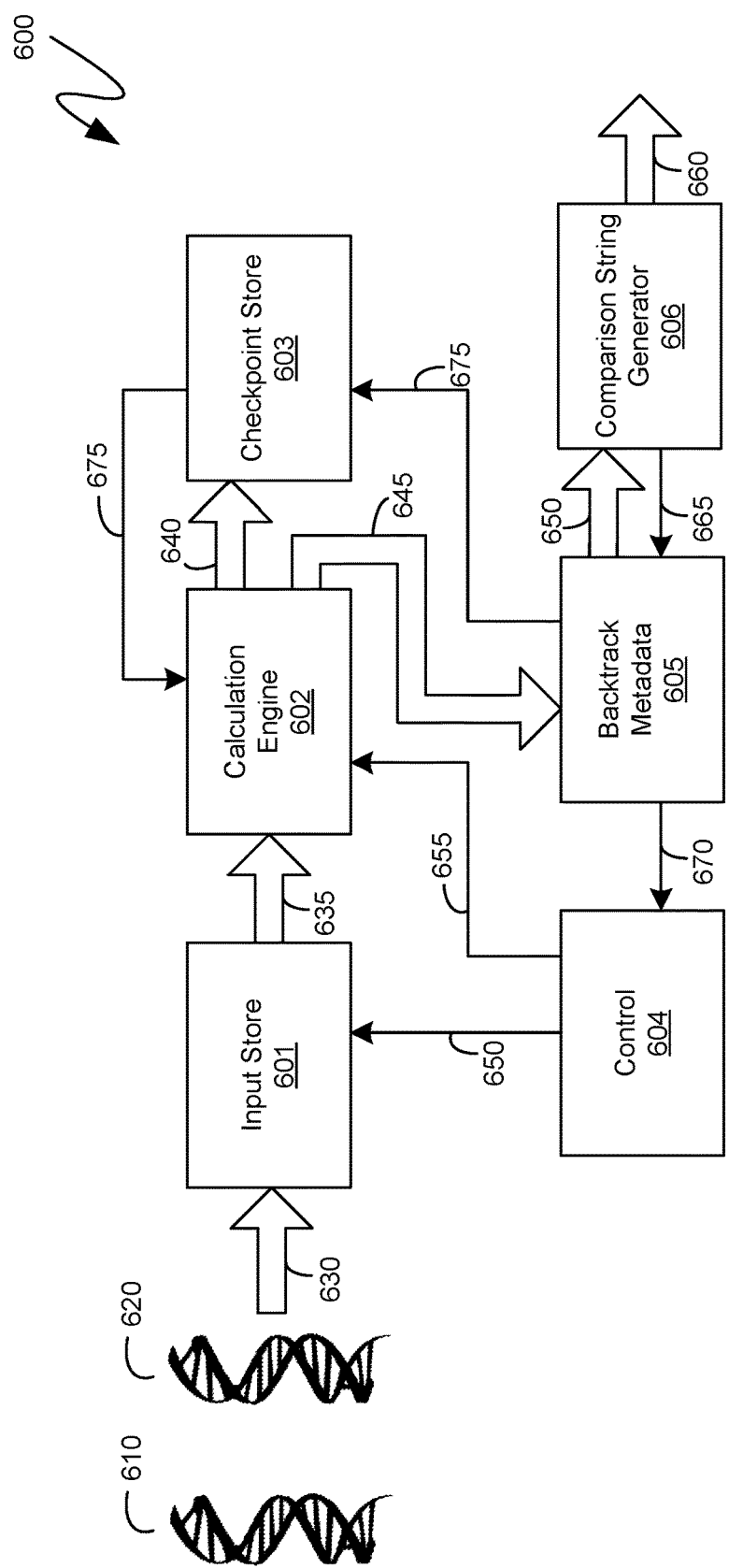
FIG. 6 is a block diagram of an aspect of an exemplary customized integrated circuit for comparing two nucleotides in a reduced memory footprint.

Turning to FIG. 6, the exemplary system 600 shown therein illustrates various components, or collections of integrated circuitry, which can, together, comprise a customized integrated circuit that can compare nucleotide sequences in a reduced memory footprint. Initially, two nucleotide sequences, such as exemplary nucleotide sequences 610 and 620 can be received as input and stored in an input store 601, as graphically represented by the arrow 630. The exemplary input store 601 can comprise integrated circuitry for the storage of digital data, such as in a manner well known to those skilled in the art. Additionally, while nucleotide sequences 610 and 620 are graphically represented by a double helix, those of skill in the art will recognize that typically only one half of such a double helix will be utilized for purposes of nucleotide sequence comparisons. The nucleotide sequences being compared, such as exemplary nucleotide sequences 610 and 620, can be obtained through any of a variety of means, typically involving specialized hardware for the extraction of genetic material.

In addition to storing the nucleotide sequences being compared, the input store 601 can also store various user settings or user input relevant to the comparison of the two nucleotide sequences. For example, as described in detail above, a gap-scoring factor can be a variable whose value can be based on various user-specific requirements in comparing the two nucleotide strings. Consequently, one or more gap-scoring factors can be specified, either directly by a user, or can be derived based upon other user input, and such gap-scoring factors can be stored, in the form of digital data, in the circuitry comprising the input store 601. When such gap-scoring factors are then to be utilized by the calculation engine 602, to generate a score for a cell selected by the control unit 604, the relevant gap-scoring factors can be among the data provided to the calculation engine 602, by the input store 601, such as is graphically represented by the arrow 635.

A calculation engine, such as the exemplary calculation engine 602, can comprise integrated circuitry that can facilitate the performance of the above-described generation of scores for individual cells in a two-dimensional matrix whose dimensions are defined by the nucleotides, of the nucleotide sequences 610 and 620, as stored in the input store 601. As detailed above, the generation of a score for an individual cell of a two-dimensional matrix can be the largest value as among: (1) the scores of one or more horizontally prior cells, (2) the scores of one or more vertically prior cells, or (3) the score of a diagonally prior cell as summed to a value that is dependent upon whether or not the nucleotides, corresponding to the cell whose score is being generated, match one another.

The operation of the calculation engine 602 can be controlled by a control component, such as the exemplary control unit 604. The exemplary control unit 604 can comprise integrated circuitry that can facilitate the selection of the relevant nucleotides, from the nucleotide sequences 610 and 620, as stored in the input store 210, and can then further facilitate the provision of such a corresponding pair of nucleotides to the calculation engine 602 for purposes of generating a score for a cell. This selection is graphically represented by the arrow 650 in FIG. 6. According to one aspect, the calculation engine 602 can generate the scores of individual cells in a serial manner. With reference back to FIG. 1, the calculation engine 602 can, for example, first generate the score 131, for the cell 151, then generate the score 132, for the cell 152, then the score 133, for the cell 153, and so on. According to another aspect, the calculation engine 602 can generate the scores of multiple cells in parallel. Again, with reference back to FIG. 1, the calculation engine 602 can, for example, first generate the score 131, for the cell 151, and can then generate the scores 134 and 132, for the cells 154 and 152, respectively, at the same time and in parallel with one another, since, as will be recognized by those skilled in the art, the inputs required to generate the score 132, of the cell 154, do not include the score 132, of the cell 152, and, vice versa, thereby enabling the scores 134 and 132 to be generated in parallel. Similarly, after the generation of the scores 134 and 132 in parallel, the calculation engine 602 can generate the scores 137, 135 and 133, for the cells 157, 155 and 153, again in parallel. As can be seen, the cells whose scores can be generated in parallel can be oriented along diagonals that extend from the lower left to the upper right of the two-dimensional matrix. Such diagonals are often termed "anti-diagonals" in the nucleotide comparison arts. Returning back to FIG. 6, the specification of which cells are to have their scores and backtrack metadata generated, as well as other like control instructions, can be provided by the control unit 604 to the cultivation engine 602, as graphically illustrated by the arrow 655.

In addition to generating scores of cells, the calculation engine 602 can also generate backtrack metadata of cells, such as in the manner detailed above. As with the generation of scores of cells, the generation of backtrack metadata can, likewise, proceed in series, one cell at a time, or can be performed in parallel, with the backtrack metadata for multiple cells being generated simultaneously. Once the calculation engine 602 has completed generating scores and backtrack metadata for one or more cells, such a scores and backtrack metadata, and the one or more cells to which they apply, can be communicated to a score aggregator unit (not illustrated in FIG. 6 for visual clarity) for storage. According to one aspect, the score aggregator unit can comprise integrated circuitry that can facilitate the storage of digital data representative of a two-dimensional matrix. As such, the score aggregator unit can receive scores and backtrack metadata of individual cells from the calculation engine, as well as generating and retaining additional information about the two-dimensional matrix or individual cells thereof. For example, the score aggregator unit can maintain a continuously updated value reflective of the highest score generated for a cell thus far by the calculation engine. Additionally, the score aggregator unit can maintain the indices, or coordinates, within the two-dimensional matrix, of the cell whose score is currently the highest score. As another example, the score aggregator unit can maintain the second-highest score, and coordinates of the corresponding cell. As detailed above, such cells can identify starting points for the backtracking mechanisms.

The backtrack metadata for cells of a subsection of the two-dimensional matrix can be retained by the backtrack metadata unit 605. For example, initially the backtrack metadata for cells of a subsection of the two-dimensional matrix that comprises the cell having the largest score can be stored by the backtrack metadata unit 605. The receipt of such backtrack metadata, for the cells of that subsection of the two-dimensional matrix, is illustrated by the arrow 645. According to one aspect, the calculation engine 602 can provide the backtrack metadata of all of the cells to the backtrack metadata unit 605 and the backtrack metadata unit 605 can discard, or not retain, the backtrack metadata of cells other than cells in the subsection of the two-dimensional matrix that comprises the cell having the largest score, which, as indicated previously, can be a subsection from which a backtracking procedure can commence. According to an alternative aspect, the calculation engine 602 can provide the backtrack metadata of only the cells of the subsection of the two-dimensional matrix being stored by the backtrack metadata unit 605. Such cells can be identified to the calculation engine 602, either by the backtrack metadata unit 605 itself, or via the control unit 604.

In a similar manner, the scores of specific cells selected as checkpoint cells can be retained by the checkpoint store 603. According to one aspect, the calculation engine 602 can provide the scores of all of the cells to the checkpoint store 603 and the checkpoint store 603 can discard, or not retain, the scores of cells other than cells selected, such as in the manner detailed above, to be checkpoint cells. According to an alternative aspect, the calculation engine 602 can provide, to the checkpoint store 603, the scores of only the cells selected to be checkpoint cells. Such cells can be identified to the calculation engine 602, either by the checkpoint store 603 itself, or via the control unit 604. The provision of scores of cells, by the calculation engine 602, to the checkpoint store 603, is represented by the arrow 640.

According to one aspect, a comparison string generator, such as the exemplary comparison string generator 606 can generate a textual string comprising indicators of similarities and differences of the pair of nucleotide sequences. By way of a simple example such as string could be in the form of "M20I5M10D6," which can signify that the first twenty nucleotides of two nucleotide sequences, which are being compared to one another, match, subsequently in insertion of five nucleotides is required to get the first nucleotide sequence to match the second nucleotide sequence, subsequent to that insertion another ten nucleotides match, followed by a deletion of six nucleotides to get the first nucleotide sequence to match the second nucleotide sequence. As indicated previously, such a comparison string can be generated by backtracking through a two-dimensional matrix, in accordance with backtrack metadata of cells of the two-dimensional matrix that was generated in the manner detailed above. Consequently, the comparison string generator 606 can request the backtrack metadata of selected cells of the two-dimensional matrix. Such a request can be directed to the backtrack metadata unit 605, as represented by the arrow 665. In response, the backtrack metadata unit 605 can provide the backtrack metadata of the selected cells, to the comparison string generator 606, as illustrated by the arrow 650. From such backtrack metadata, the comparison string generator 606 can generate a textual string comprising indicators of similarities and differences of the pair of nucleotide sequences being compared, as represented by the output 660.

As indicated previously, and is described in detail above, the backtrack metadata unit 605 can store backtrack metadata for only a portion of the cells of the two-dimensional matrix to reduce memory consumption. Should the comparison string generator 606 request backtrack metadata of one or more cells that are in a subsection of the two-dimensional matrix that is not currently stored, the backtrack metadata unit 605 can request the calculation engine 602 to regenerate the backtrack metadata of the cells of that subsection. Such a request can be directed to the control unit 604, as illustrated by the arrow 670. Additionally, the backtrack metadata unit 605 can obtain the scores of the relevant checkpoint cells, namely the checkpoint cells comprising at least some of the boundaries of an appropriate subsection of the two-dimensional matrix, from the checkpoint store 603, as illustrated by the arrow 675. The scores of such checkpoint cells can, according to one aspect, the provided to the cultivation engine 602, directly from the checkpoint store 603, in response to the request from the backtrack metadata unit 605, as illustrated by the arrow 675.

Figure 7:
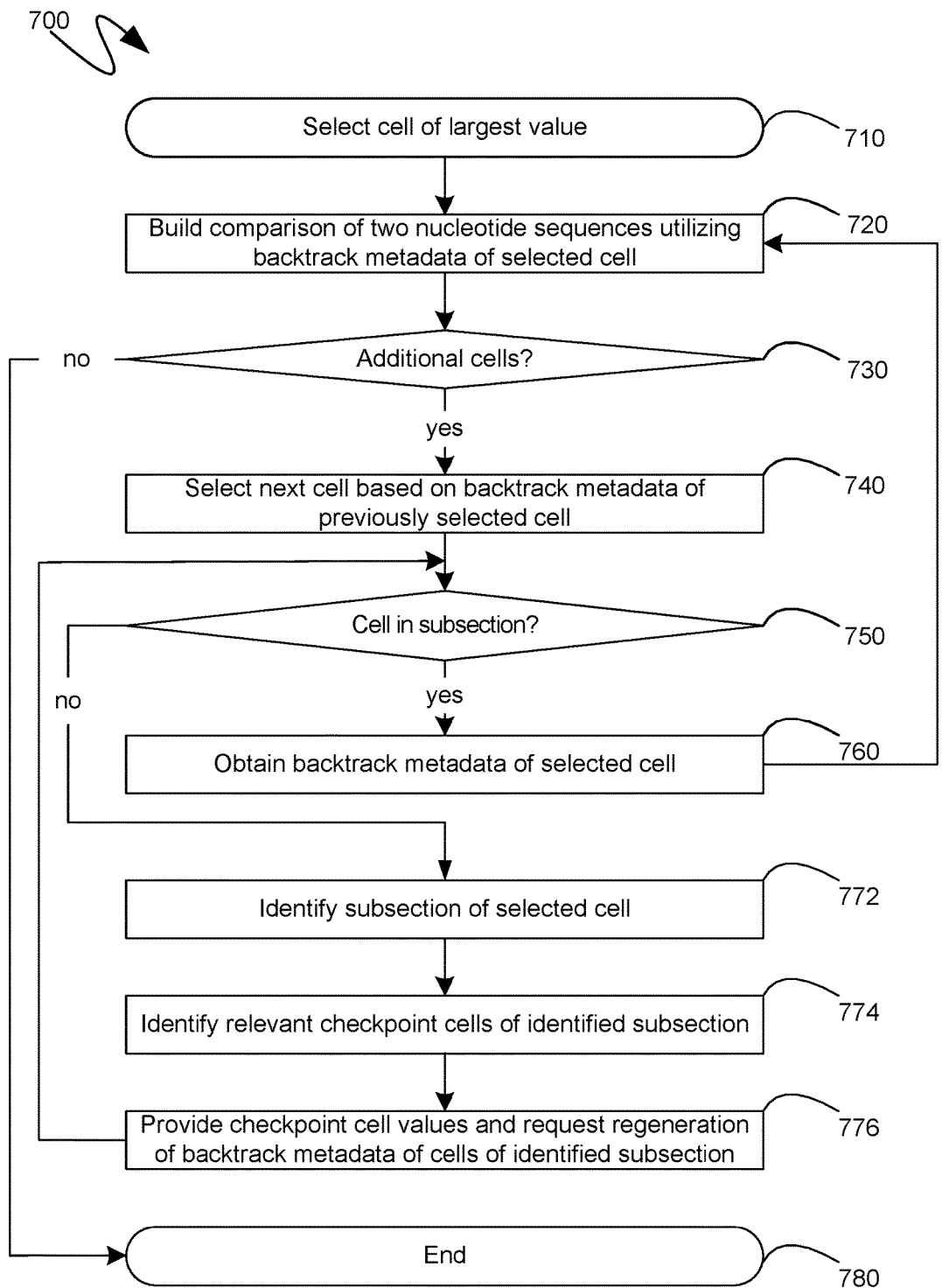
FIG. 7 is a flow diagram of the operation of an exemplary customized integrated circuit for generating nucleotide comparisons in a reduced memory footprint.

Turning to FIG. 7, the flow diagram 700 shown therein illustrates an exemplary sequence of steps, such as can be performed by the comparison string generator 606 and the backtrack metadata unit 605, both shown in FIG. 6. Initially, as illustrated by step 710, a cell of the two-dimensional matrix having the largest value, or score, can be selected from which to commence backtracking through the two-dimensional matrix for purposes of generating a textual string comprising indicators of similarities and differences of the pair of nucleotide sequences being compared. Subsequently, at step 720, such a comparison can be built with the backtrack metadata of a selected cell, such as the cell selected at step 710. At step 730, determination can be made as to whether there are additional cells, or whether the backtracking has reached the edge of the two-dimensional matrix. If there are no additional cells, as determined at step 730, the relevant processing can end at step 780.

Conversely, if, at step 730, there are additional cells whose backtrack metadata is to be taken into account in generating the aforementioned textual string, then processing can proceed with step 740 and the next cell can be selected, as identified by the backtrack metadata of the currently selected cell, such as the cell selected at step 710, or selected during a prior iteration of step 740. Subsequently, if the cell, selected at step 740, is in a subsection of the two-dimensional matrix for whose cells the backtrack metadata is currently stored, such as determined at step 750, processing can proceed to step 760 and the backtrack metadata of that cell can be obtained. Processing can then return to step 720 to update the comparison being generated in the form of the textual string. Conversely, if, at step 750, it is determined that the selected cell is part of a different subsection, namely a subsection whose cells' backtrack metadata is not currently retained in memory, processing can proceed to step 772, at which point the subsection of the two-dimensional matrix comprising the cell, selected at step 740, can be identified. Subsequently, at step 774, the checkpoint cells of the subsection identified at step 772, can be identified. As described in detail above, such checkpoint cells can comprise the cells along the border, or edge, row and column of the identified subsection. At step 776, then, the values, or scores, of the identified checkpoint cells, that were identified at step 774, together with an identification of some or all of the cells of the subsection identified at step 772, can be utilized to request that the backtrack metadata of the cells of the subsection identified at step 772 be regenerated. Processing can then return to step 750, at which point the selected cell now will be in the subsection whose cells have their backtrack metadata stored in memory. Processing can then proceed in the manner already described.

While described within the context of customized integrated circuitry, such as on an FPGA chip or ASIC, the mechanisms described herein can, likewise, be implemented by a computing device that can either comprise such customized integrated circuitry, or which can perform the aforedescribed steps on a conventional general-purpose processing unit. Consequently, turning to FIG. 8, an exemplary computing device 800 is shown therein comprising one or more general-purpose processing units, such as the exemplary CPU 820, an exemplary customized integrated circuit 850, as well as a system memory 830, and a system bus 821 that couples various system components including the system memory to the processing unit 820 and the customized integrated circuit 850. The system bus 821 may be any of several types of bus structures including a memory bus or memory controller, a peripheral bus, and a local bus using any of a variety of bus architectures. Depending on the specific physical implementation, one or more of the CPUs 820, the customized integrated circuit 850, the system memory 830 and other components of the computing device 800 can be physically co-located, such as on a single chip or silicon die or on a single circuit board. In such a case, some or all of the system bus 821 can be nothing more than silicon pathways within a single chip structure or on a single die and its illustration in FIG. 8 can be nothing more than notational convenience for the purpose of illustration.

The computing device 800 also typically includes computer readable media, which can include any available media that can be accessed by computing device 800 and includes both volatile and nonvolatile media and removable and non-removable media. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 800. Computer storage media, however, does not include communication media. Communication media embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of the any of the above should also be included within the scope of computer readable media.

Figure 8:
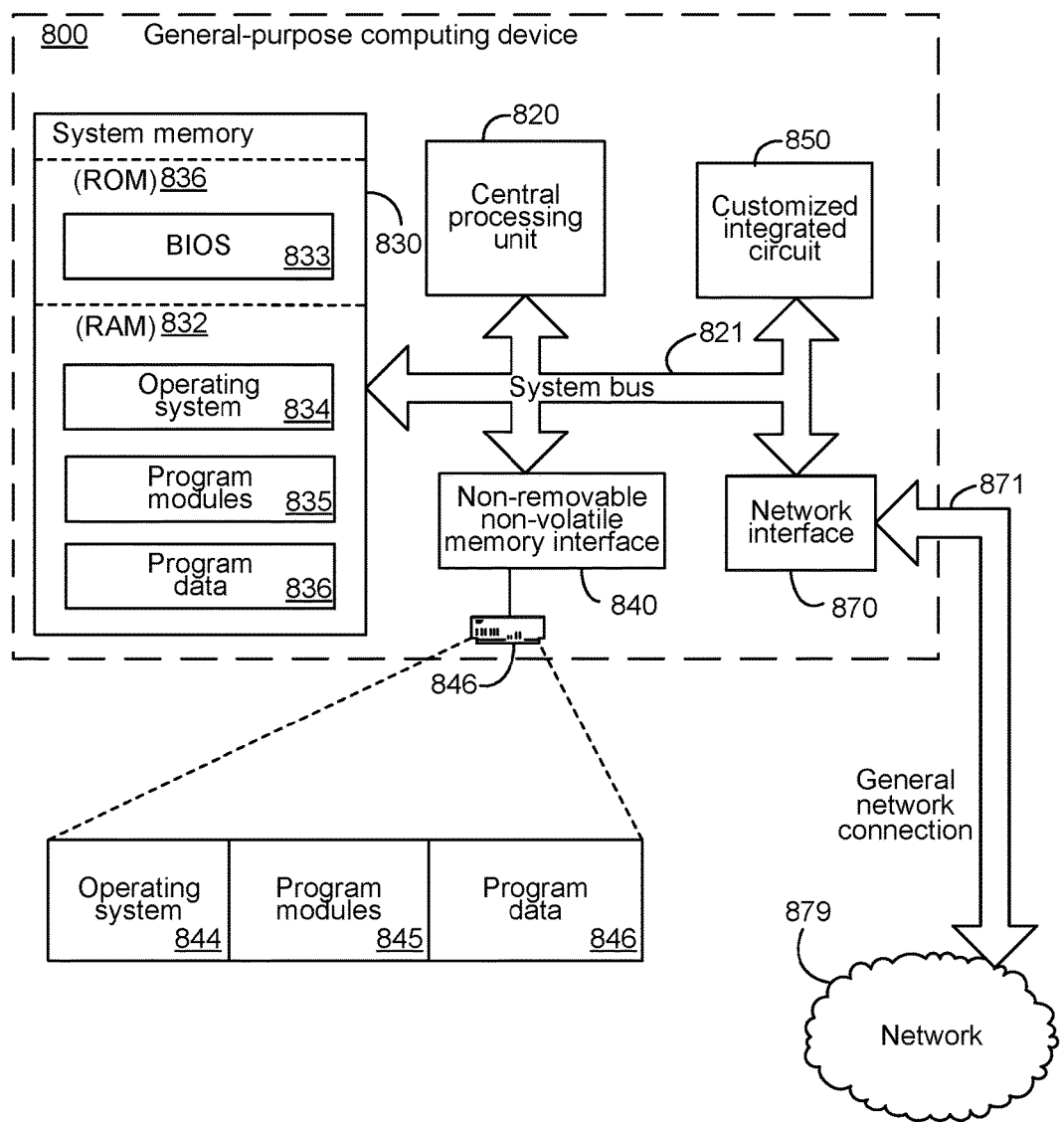
FIG. 8 is a block diagram of an exemplary computing device in which the exemplary customized circuit could be integrated.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computing device 800, such as during start-up, is typically stored in ROM 831. RAM 832 typically contains data and/or program modules that are immediately accessible to and/or presently being operated on by processing unit 820. By way of example, and not limitation, FIG. 8 illustrates operating system 834, other program modules 835, and program data 836.

The computing device 800 may also include other removable/non-removable, volatile/nonvolatile computer storage media. By way of example only, FIG. 8 illustrates a hard disk drive 841 that reads from or writes to non-removable, nonvolatile magnetic media. Other removable/non-removable, volatile/nonvolatile computer storage media that can be used with the exemplary computing device include, but are not limited to, magnetic tape cassettes, flash memory cards, digital versatile disks, digital video tape, solid state RAM, solid state ROM, and other computer storage media, as defined and delineated above. The hard disk drive 841 is typically connected to the system bus 821 through a non-volatile memory interface such as interface 840.

The drives and their associated computer storage media discussed above and illustrated in FIG. 8, provide storage of computer readable instructions, data structures, program modules and other data for the computing device 800. In FIG. 8, for example, hard disk drive 841 is illustrated as storing operating system 844, other program modules 845, and program data 846. Note that these components can either be the same as or different from operating system 834, other program modules 835 and program data 836. Operating system 844, other program modules 845 and program data 846 are given different numbers hereto illustrate that, at a minimum, they are different copies.

The computing device 800 may operate in a networked environment using logical connections to one or more remote computers. The computing device 800 is illustrated as being connected to the general network connection 871 through a network interface or adapter 870, which is, in turn, connected to the system bus 821. In a networked environment, program modules depicted relative to the computing device 800, or portions or peripherals thereof, may be stored in the memory of one or more other computing devices that are communicatively coupled to the computing device 100 through the general network connection 871. It will be appreciated that the network connections shown are exemplary and other means of establishing a communications link between computing devices may be used.

Although described as a single physical device, the exemplary computing device 800 can be a virtual computing device, in which case the functionality of the above-described physical components, such as the CPU 820, the system memory 830, the network interface 870, and other like components can be provided by computer-executable instructions. Such computer-executable instructions can execute on a single physical computing device, or can be distributed across multiple physical computing devices, including being distributed across multiple physical computing devices in a dynamic manner such that the specific, physical computing devices hosting such computer-executable instructions can dynamically change over time depending upon need and availability. In the situation where the exemplary computing device 800 is a virtualized device, the underlying physical computing devices hosting such a virtualized computing device can, themselves, comprise physical components analogous to those described above, and operating in a like manner. Furthermore, virtual computing devices can be utilized in multiple layers with one virtual computing device executed within the construct of another virtual computing device. The term "computing device", therefore, as utilized herein, means either a physical computing device or a virtualized computing environment, including a virtual computing device, within which computer-executable instructions can be executed in a manner consistent with their execution by a physical computing device. Similarly, terms referring to physical components of the computing device, as utilized herein, mean either those physical components or virtualizations thereof performing the same or equivalent functions.

The descriptions above include, as a first example, a customized integrated circuit comprising: a calculation engine comprising circuitry that, during operation of the customized integrated circuit, enables the customized integrated circuit to: generate, for individual cells of a two-dimensional matrix, scores that are based on generated scores of prior cells and individual nucleotides, from each of a pair of nucleotide sequences that are being compared to one another, that individually correspond to the individual cells; and generate backtrack metadata for the individual cells based at least in part on the generating of the scores; and a backtrack metadata unit comprising circuitry that, during operation of the customized integrated circuit, enables the customized integrated circuit to: store backtrack metadata of cells of only a first subsection of the two-dimensional matrix; obtain, from the stored backtrack metadata, a first backtrack metadata of a first cell of the two-dimensional matrix if the first cell is in the first subsection; request the calculation engine to generate again backtrack metadata of cells of only a second subsection of the two-dimensional matrix, based on scores of cells of the two-dimensional matrix that comprise two edges of the second subsection, if the first cell is in the second subsection, the second subsection being mutually exclusive of the first subsection; and obtain, from the regenerated backtrack metadata, the first backtrack metadata of the first cell of the two-dimensional matrix if the first cell is in the second subsection.

A second example is the customized integrated circuit of the first example, wherein the calculation engine generates scores for the cells in the two-dimensional matrix in series, one cell at a time.

A third example is the customized integrated circuit of the first example, wherein the calculation engine generates scores for the cells in the two-dimensional matrix in parallel, generating scores for multiple cells at a same time.

A fourth example is the customized integrated circuit of the first example, further comprising a comparison string generator comprising circuitry that, during operation of the customized integrated circuit, enables the customized integrated circuit to: select the first cell; request the first backtrack metadata of the first cell from the backtrack metadata unit; and modify a textual string in accordance with the first backtrack metadata, the textual string comprising indicators of similarities and differences of the pair of nucleotide sequences that are being compared to one another.

A fifth example is the customized integrated circuit of the fourth example, further comprising a score aggregation unit comprising circuitry that, during operation of the customized integrated circuit, enables the customized integrated circuit to: receive scores of cells of the two-dimensional matrix as generated by the calculation engine; retain a coordinates, within the two-dimensional matrix, of a highest score cell having a score that is greater in value than scores of other cells of the two-dimensional matrix.

A sixth example is the customized integrated circuit of the fifth example, wherein the selecting is informed by the retained coordinates.

A seventh example is the customized integrated circuit of the fourth example, wherein the comparison string generator comprises further circuitry that, during operation of the customized integrated circuit, enables the customized integrated circuit to: select subsequent cells based on backtrack metadata of previously selected cells; and repeat the requesting and the modifying for the subsequent cells.

An eighth example is the customized integrated circuit of the first example, further comprising a checkpoint store unit comprising circuitry that, during operation of the customized integrated circuit, enables the customized integrated circuit to either: receive scores, as generated by the calculation engine, of cells of the two-dimensional matrix and then discard those of cells other than checkpoint cells; or request scores, as generated by the calculation engine, only of checkpoint cells of the two-dimensional matrix; wherein checkpoint cells are cells of the two-dimensional matrix that comprise edges of mutually exclusive subsections of the two-dimensional matrix, the mutually exclusive subsections comprising both the first and second subsections.

A ninth example is the customized integrated circuit of the eighth example, wherein the mutually exclusive subsections of the two-dimensional matrix are each a same size, except for subsections at two edges of the two-dimensional matrix that are remnants left over after a rest of the two-dimensional matrix was subdivided into the mutually exclusive subsections of the same size.

A tenth example is the customized integrated circuit of the ninth example, wherein the remnant subsections are at an opposite side of the two-dimensional matrix from the first subsection initially stored by the backtrack metadata unit.

An eleventh example the customized integrated circuit of the first example: wherein the first backtrack metadata comprises a first two-digit binary value indicative of a directional assignment associated with the first cell, a first one-digit binary value indicative of whether the first cell is part of a deletion stretching across multiple contiguous cells, and a second one-digit binary value indicative of whether the first cell is part of an insertion stretching across multiple contiguous cells.

A twelfth example is the customized integrated circuit of the first example, wherein the backtrack metadata unit comprises further circuitry that, during operation of the customized integrated circuit, enables the customized integrated circuit to: store backtrack metadata of cells of only the first subsection of the two-dimensional matrix in a same memory in which the backtrack metadata of cells of only the first subsection of the two-dimensional matrix was stored.

A thirteenth example is the customized integrated circuit of the first example, wherein the backtrack metadata unit comprises further circuitry that, during operation of the customized integrated circuit, enables the customized integrated circuit to either: receive backtrack metadata, as generated by the calculation engine, of cells of the two-dimensional matrix and then discard those of cells other than cells of the first subsection; or request scores, as generated by the calculation engine, only of cells of the first subsection.

A fourteenth example is the customized integrated circuit of the first example, wherein the customized integrated circuit is an FPGA device.

A fifteenth example is a computing device comprising: one or more processing units; and one or more computer-readable storage media comprising computer-executable instructions, which, when executed by the one or more processing units, cause the computing device to: generate, for individual cells of a two-dimensional matrix, scores that are based on generated scores of prior cells and individual nucleotides, from each of a pair of nucleotide sequences that are being compared to one another, that individually correspond to the individual cells; generate backtrack metadata for the individual cells based at least in part on the generating of the scores; discard generated backtrack metadata except for backtrack metadata of cells of a first subsection of the two-dimensional matrix; obtain a first backtrack metadata of a first cell of the two-dimensional matrix if the first cell is in the first subsection; generate again backtrack metadata of cells of only a second subsection of the two-dimensional matrix, based on scores of cells of the two-dimensional matrix that comprise two edges of the second subsection, if the first cell is in the second subsection, the second subsection being mutually exclusive of the first subsection; and obtain, from the regenerated backtrack metadata, the first backtrack metadata of the first cell of the two-dimensional matrix if the first cell is in the second subsection.

A sixteenth example is the computing device of the fifteenth example, wherein the computer-readable storage media comprise further computer-executable instructions, which, when executed by the one or more processing units, cause the computing device to: modify a textual string in accordance with the first backtrack metadata, the textual string comprising indicators of similarities and differences of the pair of nucleotide sequences that are being compared to one another.

A seventeenth example is the computing device of the fifteenth example, wherein the computer-readable storage media comprise further computer-executable instructions, which, when executed by the one or more processing units, cause the computing device to: discard generated scores of cells other than checkpoint cells, wherein checkpoint cells are cells of the two-dimensional matrix that comprise edges of mutually exclusive subsections of the two-dimensional matrix, the mutually exclusive subsections comprising both the first and second subsections.

An eighteenth example is the computing device of the seventeenth example, wherein the mutually exclusive subsections of the two-dimensional matrix are each a same size, except for subsections at two edges of the two-dimensional matrix that are remnants left over after a rest of the two-dimensional matrix was subdivided into the mutually exclusive subsections of the same size.

A nineteenth example is the computing device of the fifteenth example: wherein the first backtrack metadata comprises a first two-digit binary value indicative of a directional assignment associated with the first cell, first one-digit binary value indicative of whether the first cell is part of a deletion stretching across multiple contiguous cells, and a second one-digit binary value indicative of whether the first cell is part of an insertion stretching across multiple contiguous cells.

A twentieth example is a method of generating, by a computing device, a textual string comprising indicators of similarities and differences of a first nucleotide sequence as compared with a second nucleotide sequence, the method comprising: generating, on the computing device, for individual cells of a two-dimensional matrix, scores that are based on generated scores of prior cells and individual nucleotides, from each of the first and second nucleotide sequences, that individually correspond to the individual cells; generating, on the computing device, backtrack metadata for the individual cells based at least in part on the generating of the scores; discarding, from the computing device, generated backtrack metadata except for backtrack metadata of cells of a first subsection of the two-dimensional matrix; obtaining, with the first computing device, a first backtrack metadata of a first cell of the two-dimensional matrix if the first cell is in the first subsection; generating again, on the computing device, backtrack metadata of cells of only a second subsection of the two-dimensional matrix, based on scores of cells of the two-dimensional matrix that comprise two edges of the second subsection, if the first cell is in the second subsection, the second subsection being mutually exclusive of the first subsection; and obtaining, with the first computing device, from the regenerated backtrack metadata, the first backtrack metadata of the first cell of the two-dimensional matrix if the first cell is in the second subsection.

As can be seen from the above descriptions, customized integrated circuits for comparing two nucleotide sequences in a reduced memory footprint have been presented. In view of the many possible variations of the subject matter described herein, we claim as our invention all such embodiments as may come within the scope of the following claims and equivalents thereto.

We claim:
1. A customized integrated circuit comprising:
a calculation engine comprising circuitry that, during operation of the customized integrated circuit, enables the customized integrated circuit to:
generate, for individual cells of a two-dimensional matrix, scores that are based on generated scores of prior cells and pairs of nucleotides that correspond to the individual cells, wherein the pairs of nucleotides each comprise one nucleotide from each of a first nucleotide sequence and a second nucleotide sequence that are being compared to one another; and
generate backtrack metadata for the individual cells based at least in part on the generating of the scores; and
a backtrack metadata unit comprising circuitry that, during operation of the customized integrated circuit, enables the customized integrated circuit to:
store, in a cache, backtrack metadata of cells of only a first subsection of the two-dimensional matrix;

determine that a first cell of the two-dimensional matrix, for which the backtrack metadata unit is to output a first backtrack metadata, is not in the first subsection;

request, in response to the determining, the calculation engine to generate again backtrack metadata of cells of only a second subsection of the two-dimensional matrix, the calculation engine regenerating the backtrack metadata of the cells of only the second subsection based on scores of cells of the two-dimensional matrix that comprise two edges of the second subsection, the second subsection being mutually exclusive of the first subsection; and obtain, from the regenerated backtrack metadata of the cells of only the second subsection, stored in the cache, the first backtrack metadata of the first cell;

wherein the customized integrated circuit is utilized in the comparing of the first and second nucleotide sequences, the comparing comprising generating a textual string comprising indicators of similarities and differences of the first nucleotide sequence as compared with the second nucleotide sequence.

2. The customized integrated circuit of claim 1, wherein the calculation engine generates scores for the cells in the two-dimensional matrix in series, one cell at a time.

3. The customized integrated circuit of claim 1, wherein the calculation engine generates scores for the cells in the two-dimensional matrix in parallel, generating scores for multiple cells at a same time.

4. The customized integrated circuit of claim 1, further comprising a comparison string generator comprising circuitry that, during operation of the customized integrated circuit, enables the customized integrated circuit to:

select the first cell;

request the first backtrack metadata of the first cell from the backtrack metadata unit; and modify the textual string in accordance with the first backtrack metadata.

5. The customized integrated circuit of claim 4, further comprising a score aggregation unit comprising circuitry that, during operation of the customized integrated circuit, enables the customized integrated circuit to:

receive scores of cells of the two-dimensional matrix as generated by the calculation engine;

retain a coordinates, within the two-dimensional matrix, of a highest score cell having a score that is greater in value than scores of other cells of the two-dimensional matrix.

6. The customized integrated circuit of claim 5, wherein the selecting is informed by the retained coordinates.

7. The customized integrated circuit of claim 4, wherein the comparison string generator comprises further circuitry that, during operation of the customized integrated circuit, enables the customized integrated circuit to:

select subsequent cells based on backtrack metadata of previously selected cells; and repeat the requesting and the modifying for the subsequent cells.

8. The customized integrated circuit of claim 1, further comprising a checkpoint store unit comprising circuitry that, during operation of the customized integrated circuit, enables the customized integrated circuit to either:

receive scores, as generated by the calculation engine, of cells of the two-dimensional matrix and then discard those of cells other than checkpoint cells; or request scores, as generated by the calculation engine, only of checkpoint cells of the two-dimensional matrix;

wherein checkpoint cells are cells of the two-dimensional matrix that comprise edges of mutually exclusive subsections of the two-dimensional matrix, the mutually exclusive subsections comprising both the first and second subsections.

9. The customized integrated circuit of claim 8, wherein the mutually exclusive subsections of the two-dimensional matrix are each a same size, except for subsections at two edges of the two-dimensional matrix that are remnants left over after a rest of the two-dimensional matrix was subdivided into the mutually exclusive subsections of the same size.

10. The customized integrated circuit of claim 9, wherein the remnant subsections are at an opposite side of the two-dimensional matrix from the first subsection initially stored by the backtrack metadata unit.

11. The customized integrated circuit of claim 1, wherein the first backtrack metadata comprises a first two-digit binary value indicative of a directional assignment associated with the first cell, a first one-digit binary value indicative of whether the first cell is part of a deletion stretching across multiple contiguous cells, and a second one-digit binary value indicative of whether the first cell is part of an insertion stretching across multiple contiguous cells.

12. The customized integrated circuit of claim 1, wherein the backtrack metadata unit comprises further circuitry that, during operation of the customized integrated circuit, enables the customized integrated circuit to either:

receive backtrack metadata, as generated by the calculation engine, of cells of the two-dimensional matrix and then discard those of cells other than cells of the first subsection; or request scores, as generated by the calculation engine, only of cells of the first subsection.

13. The customized integrated circuit of claim 1, further comprising the cache, the cache being an on-chip cache, the customized integrated circuit being packaged as a chip.

14. One or more computing devices comprising one or more processing units; and one or more computer-readable storage media comprising computer-executable instructions, which, when executed by the one or more processing units, cause the one or more computing devices to:

generate, for individual cells of a two-dimensional matrix, scores that are based on generated scores of prior cells and pairs of nucleotides that correspond to the individual cells, wherein the pairs of nucleotides each comprise one nucleotide from each of a first nucleotide sequence and a second nucleotide sequence that are being compared to one another;

generate backtrack metadata for the individual cells based at least in part on the generating of the scores;

store, in a cache, backtrack metadata of cells of only a first subsection of the two-dimensional matrix;

generate again backtrack metadata of cells of only a second subsection of the two-dimensional matrix, based on scores of cells of the two-dimensional matrix that comprise two edges of the second subsection, if a first cell, for which a first backtrack metadata is to be determined, is in the second subsection, the second subsection being mutually exclusive of the first subsection;

obtain, from the regenerated backtrack metadata of the cells of only the second subsection, stored in the cache, the first backtrack metadata of the first cell of the two-dimensional matrix; and generate a textual string comprising indicators of similarities and differences of the first nucleotide sequence as compared with the second nucleotide sequence.

15. The one or more computing devices of claim 14, wherein the computer-readable storage media comprise further computer-executable instructions, which, when executed by the one or more processing units, cause the one or more computing devices to:
   modify the textual string in accordance with the first backtrack metadata.

16. The one or more computing devices of claim 14, wherein the computer-readable storage media comprise further computer-executable instructions, which, when executed by the one or more processing units, cause the one or more computing devices to:
   discard generated scores of cells other than checkpoint cells, wherein checkpoint cells are cells of the two-dimensional matrix that comprise edges of mutually exclusive subsections of the two-dimensional matrix, the mutually exclusive subsections comprising both the first and second subsections.

17. The one or more computing devices of claim 16, wherein the mutually exclusive subsections of the two-dimensional matrix are each a same size, except for subsections at two edges of the two-dimensional matrix that are remnants left over after a rest of the two-dimensional matrix was subdivided into the mutually exclusive subsections of the same size.

18. The one or more computing devices of claim 14, wherein the first backtrack metadata comprises a first two-digit binary value indicative of a directional assignment associated with the first cell, first one-digit binary value indicative of whether the first cell is part of a deletion stretching across multiple contiguous cells, and a second one-digit binary value indicative of whether the first cell is part of an insertion stretching across multiple contiguous cells.

19. The one or more computing device of claim 14, wherein the cache is an on-chip cache of one of the one or more processing units.

20. A method of comparing nucleotide sequences with one or more computing devices, the method comprising:
   generating, on the one or more computing devices, for individual cells of a two-dimensional matrix, scores that are based on generated scores of prior cells and pairs of nucleotides that correspond to the individual cells, wherein the pairs of nucleotides each comprise one nucleotide from each of a first nucleotide sequence and a second nucleotide sequence that are being compared to one another;
   generating, on the one or more computing devices, backtrack metadata for the individual cells based at least in part on the generating of the scores;
   storing, in a cache on at least one of the one or more computing devices, backtrack metadata of cells of only a first subsection of the two-dimensional matrix;
   generating again, on the one or more computing devices, backtrack metadata of cells of only a second subsection of the two-dimensional matrix, based on scores of cells of the two-dimensional matrix that comprise two edges of the second subsection, if a first cell, for which a first backtrack metadata is to be determined, is in the second subsection, the second subsection being mutually exclusive of the first subsection;
   obtaining, with the one or more computing devices, from the regenerated backtrack metadata of the cells of only the second subsection, stored in the cache, the first backtrack metadata of the first cell of the two-dimensional matrix; and
   generating, by the one or more computing devices, a textual string comprising indicators of similarities and differences of the first nucleotide sequence as compared with the second nucleotide sequence.

* * * * *